(12) United States Patent
Feldchtein et al.

(10) Patent No.: US 7,428,053 B2
(45) Date of Patent: Sep. 23, 2008

(54) COMMON PATH FREQUENCY DOMAIN OPTICAL COHERENCE REFLECTOMETRY/TOMOGRAPHY DEVICE

(75) Inventors: Felix I. Feldchtein, Cleveland, OH (US); Grigory V. Gelikonov, Nizhny Novgorod (RU)

(73) Assignee: Imalux Corporation, Cleveland, OH (US)

( * ) Notice: Subject to any disclaimer, the term of this patent is extended or adjusted under 35 U.S.C. 154(b) by 162 days.

(21) Appl. No.: 11/539,719

(22) Filed: Oct. 9, 2006

(65) Prior Publication Data
US 2007/0115476 A1    May 24, 2007

Related U.S. Application Data

(63) Continuation-in-part of application No. 11/456,414, filed on Jul. 10, 2006.

(60) Provisional application No. 60/697,714, filed on Jul. 8, 2005.

(51) Int. Cl.
G01B 9/02 (2006.01)
G01B 11/02 (2006.01)

(52) U.S. Cl. .................. 356/479; 356/497

(58) Field of Classification Search .......... 356/477, 356/478, 479, 491, 497
See application file for complete search history.

(56) References Cited

U.S. PATENT DOCUMENTS

| | | | |
|---|---|---|---|
| 6,665,456 B2 * | 12/2003 | Dave et al. | 385/11 |
| 6,738,144 B1 * | 5/2004 | Dogariu | 356/479 |
| 7,042,573 B2 * | 5/2006 | Froggatt | 356/479 |
| 7,136,167 B2 * | 11/2006 | Failes | 356/479 |
| 7,177,491 B2 * | 2/2007 | Dave et al. | 385/11 |
| 2007/0103683 A1 * | 5/2007 | Wang | 356/364 |
| 2007/0236700 A1 * | 10/2007 | Yun et al. | 356/491 |

* cited by examiner

Primary Examiner—Michael A. Lyons
Assistant Examiner—Scott M Richey
(74) Attorney, Agent, or Firm—Renner, Otto, Boisselle & Sklar, LLP (57) ABSTRACT

Common path frequency domain optical coherence reflectometry/tomography devices include a portion of optical fiber with predetermined optical properties adapted for producing two eigen modes of the optical radiation propagating therethrough with a predetermined optical path length difference. The two replicas of the optical radiation outgoing from the portion of the optical fiber are then delivered to an associated sample by an optical fiber probe. The tip of the optical fiber serves as a reference reflector and also serves as a combining element that produces a combination optical radiation by combining an optical radiation returning from the associated sample with a reference optical radiation reflected from the reference reflector. The topology of the devices allows for registering a cross-polarized or a parallel-polarized component of the optical radiation reflected or backscattered from the associated sample. Having the optical path length difference for the two eigen modes of the optical radiation (which is an equivalent of an interferometer offset in previously known devices) differ from the reference offset in the devices of the present invention allows for relieving the requirements to the spectral resolution of the FD OCT engine and/or data acquisition and processing system, and substantially eliminates depth ambiguity problems.

23 Claims, 4 Drawing Sheets

COMMON PATH FREQUENCY DOMAIN OPTICAL COHERENCE REFLECTOMETRY/TOMOGRAPHY DEVICE

CROSS-REFERENCE TO RELATED APPLICATIONS

This application is a continuation-in-part of U.S. patent application Ser. No. 11/456,414 which was filed on Jul. 10, 2006, which is based on and claims priority to provisional U.S. patent application Ser. No. 60/697,714, which was filed on Jul. 8, 2005.

BACKGROUND OF THE INVENTION

The present invention relates to systems and methods for visualizing subsurface regions of samples, and more specifically, to a frequency domain optical coherence reflectometer and frequency domain optical coherence tomography (OCT) device that provides internal depth profiles and depth resolved images of samples.

Optical coherence reflectometry/tomography involves splitting an optical radiation into at least two portions, and directing one portion of the optical radiation toward a subject of investigation. The subject of investigation will be further referred to as a "sample", whereas the portion of optical radiation directed toward the sample will be further referred to as a "sample portion" of optical radiation. The sample portion of optical radiation is directed toward the sample by means of a delivering device, such as an optical probe. Another portion of the optical radiation, which will be further referred to as "reference portion", is used to provide heterodyne detection of the low intensity radiation, reflected or backscattered from the sample.

Typically, any optical coherence reflectometer or OCT device is specified by a longitudinal (in-depth) range of interest, whereas the longitudinal range of interest and the sample overlap, at least partially. The longitudinal range of interest includes a proximal boundary and a distal boundary, and in time domain systems is equivalent to the longitudinal scanning range. In traditional time domain optical coherence reflectometry, at every moment only a small part of the sample portion of the optical radiation, reflected or backscattered from some point located inside the boundaries of the longitudinal range of interest is utilized. In-depth profiling of the sample is provided by introducing a variable optical path length difference for the sample and reference portions of the optical radiation.

A well known version of time domain optical coherence reflectometry and tomography is the "common path" version, also known as autocorrelator or Fizeau interferometer based OCR/OCT. In this version, the reference and sample portions of the optical radiation do not travel along separate optical paths. Instead, a reference reflection is created in the sample optical path by introducing an optical inhomogenuity in the distal part of the delivering device, the inhomogenuity serving as a reference reflector. Resulting from that, the reference and sample portions of the optical radiation experience an axial shift only. The distance between the reference reflector and the front boundary of the longitudinal range of interest will be considered here as "reference offset". The entire combination of the sample portion of the optical radiation and axially shifted reference portion is combined with the replica of the same combination, shifted axially, so the reference portion of one replica has a time of flight (or optical path length) matching that of the sample portion of another replica. These portions interfere in a very similar way to the traditional "separate path" time domain optical coherence reflectometry/tomography embodiments. The interference signal is formed by a secondary interferometer, the two arms of which have an optical length difference ("interferometer offset") equal to the reference offset. By scanning an optical delay between the two replicas, a time profile of the interference signal is obtained, which represents the in-depth profile of the coherent part of the reflected sample optical radiation. The later is substantially equivalent to the profile obtained in traditional separate path embodiments.

Common path frequency domain reflectometry/tomography has a lot of intrinsic advantages over separate path frequency domain reflectometry/tomography. These advantages are based on the fact that reference and sample portions of the optical radiation propagate in the same optical path and therefore experience substantially identical delay, polarization distortions, optical dispersion broadening, and the like. Therefore, the interference fringes are insensitive to the majority of the probe properties, including the optical fiber probe length, dispersion properties and polarization mismatch. In separate path frequency domain reflectometry/tomography, the length and dispersion of the sampling arm should be closely matched with the reference arm and the polarization mismatch should be prevented (using PM fiber or other means) or compensated (using polarization diversity receiver or other means).

The optical spectrum of the combined reference and sample portions of the optical radiation, both in the separate path and the common path reflectometry and OCT designs has all necessary information about the in-depth coherent reflection profile by including a component that is Fourier conjugate of the in-depth profile of the sample. Thus, the profile is capable of being extracted from Fourier transformation of the optical spectrum of the combined optical radiation.

Fourier transformation of the optical spectrum of the reference and sample optical radiation combination is actually well known and has been utilized in frequency domain optical coherence reflectometry and tomography (also known as spectral domain and Fourier domain) since 1995. In frequency domain optical coherence reflectometry, the reference and sample portions of the optical radiation have a substantially similar optical path. The optical spectrum of the combined optical radiation can be registered using parallel means (such as a spectrograph) or sequential scanning means using a swept frequency optical source.

However, it took several years for the scientific community to realize that frequency domain optical coherence reflectometry/tomography has a fundamental, major advantage in signal-to-noise ratio (SNR) over traditional time-domain reflectometry/tomography. The frequency domain reflectometry/tomography SNR advantage can be explained by a simultaneous use of light coming back from all in-depth pixels, whereas in time domain reflectometry/tomography, only light from one in-depth pixel is used at a time and all the rest is wasted. Therefore, the SNR for frequency domain reflectometry/tomography is capable of being improved by a factor equal to the number of in-depth pixels (which for a system with moderate in-depth resolution of 15 μm and scanning depth of 2 mm will be a factor of 133). It should be also noted that this advantage increases with improving in-depth resolution for the same depth, reaching a factor of 1000 for 2 μm resolution.

Common path frequency domain optical coherence reflectometry and tomography are well known in the art. However, previously known devices typically employ an optical layout where reference reflection occurs in the vicinity of the sample. In these devices the combination of reference and sample reflection is directly spectrally analyzed without any additional optical processing, such as using an additional interferometer. This approach works very well if stable reference reflection can be obtained from a point axially close to the sample. Unfortunately, in many situations, and in particular, in a probe design for medical application it is very difficult or even impossible to obtain reference reflection from the vicinity of the sample and instead, reference reflection can only be obtain from a point located far from the sample.

A limitation to such common path frequency domain OCR/OCT systems without a secondary interferometer is the great value of required spectral resolution of the frequency domain OCR/OCT processing engine. This limitation becomes especially important in medical applications. The problem is that even for miniature optical fiber endoscopic probes known in the art that use the optical fiber tip of the optical fiber probe as a reference element, the reference offset could be as big as 10 mm, since the optical fiber probe inevitably includes a lens system in its distal part. This distance may be greater if a bigger probe with a larger field of view is required, such as for laparoscopy. It is known that the larger the in-depth distance is between the most remote points involved in the optical interference (which is the reference offset plus intended depth range), the finer the spectral resolution of the system should be, in order to resolve the highest frequency spectral fringes.

The later can be illustrated referring to the spectrum of two pairs of pulses with different time separation. Each pair of pulses (for OCR/OCT corresponding to a pair of reflecting surfaces separated in depth) produces interference fringes in the spectrum. The frequency of spectral fringes increases accordingly with increasing of the delay between pulses. To restore the in-depth profile, the spectral resolution of the frequency domain OCR/OCT engine should be sufficient to resolve the most frequent fringes in the optical spectrum. In spatial-temporal terminology, the effective coherence length should be sufficient to provide interference between the most distant points. Therefore, a large reference offset creates unnecessary high spectral resolution requirements for the spectrometer or unnecessary strict instantaneous line width requirements for the tunable source. It also puts an additional burden on the data acquisition and real time signal processing system, where a several times increase of data flow is required for the same image acquisition rate. Additionally, the system design would require substantial changes if another probe with different reference offset is needed. All of the described is capable of making questionable the advantage of using common path topology in a frequency domain OCR/OCT system.

One solution would be to add an additional interferometer in the manner known for time domain OCT/OCR systems. Unfortunately, applying frequency domain registration to earlier separate path OCR/OCT systems creates a serious problem—the "depth ambiguity problem" (also referred to as mirror artifact or depth degeneracy). The problem is well known and is associated with Fourier transformation's inability to differentiate between positive and negative depth coordinates in a case of the optical path difference for the interfering reference and sample portions of the optical radiation being reduced to zero. The same problem would arise for a common path frequency domain OCR/OCT system utilizing a secondary interferometer since in a system of this type, as discussed above, the interference signal is formed by reducing to zero the optical path difference for the interfering reference and sample portions of the two replicas of the optical radiation. There are several ways known to deal with the depth degeneracy problem, all of them being cost consuming and rather complicated for being used in a medical device.

Another limitation to previously known common path frequency domain reflectometry/tomography devices is that the registered interference signal is responsive only to the non-depolarized portion, or in other words, responsive only to the parallel-polarized component of the optical radiation reflected or backscattered from the associated sample. The portion of the optical radiation depolarized by the associated sample and reflected or backscattered from it (the cross-polarized component), does not produce interference fringes and is not registered. However, in many cases OCR/OCT images created from the depolarized portion of the optical radiation demonstrate enhanced contrast and could be successfully used for biomedical diagnostics.

As will be appreciated by those skilled in the art, the concept of "parallel-polarized" and "cross-polarized" is applied here for elliptical polarization. "Parallel-polarized" is used for components with elliptical polarizations having the same eccentricity, same orientation of the long axis (ellipse tilt angle), and same rotation direction for the electric field. "Cross-polarized" is used for components with elliptical polarizations having the same eccentricity, orthogonal orientation of the long axis, and opposite rotation direction for the electric field. As in the case of linear or circular polarization these parallel-polarized components produce strongest interference, while cross-polarized components do not interfere at all.

Thus, there exists a need for common path frequency domain OCR/OCT devices that use the advantages of a common path optical interferometer design together with the advantages of frequency domain registration of the optical spectrum of the combined reference and sample portions of the optical radiation, overcoming at the same time limitations of both approaches.

There also exists a need for common path frequency domain OCR/OCT devices that provide registration of the portion of the optical radiation depolarized by an associated sample, i.e. of the cross-polarized component of the optical radiation reflected or backscattered from an associated sample.

SUMMARY OF THE INVENTION

In accordance with the present invention, there are provided improved common path frequency domain OCR/OCT devices that use the advantages of a common path optical interferometer design together with the advantages of frequency domain registration of the optical spectrum of the combined reference and sample portions of the optical radiation, overcoming at the same time limitations of both approaches.

Further, in accordance with the present invention, there are provided common path frequency domain OCR/OCT devices that provide registration of a portion of the optical radiation depolarized by an associated sample, i.e. of a cross-polarized component of the optical radiation reflected or backscattered from an associated sample.

Still further, in accordance with the present invention, there are provided common path frequency domain OCR/OCT devices that provide registration of a portion of the optical radiation not depolarized by an associated sample, i.e. of a parallel-polarized component of the optical radiation reflected or backscattered from an associated sample.

According to one aspect of the present invention, a common path frequency domain optical coherence reflectometer is provided that includes a source of an optical radiation, a directional element, and a delivering device. The common path frequency domain optical coherence reflectometer is specified by a longitudinal range of interest having a proximal boundary and a distal boundary, and at least partially overlapping with an associated sample. The common path frequency domain optical coherence reflectometer also includes a portion of optical fiber with predetermined optical properties optically coupled with the source of optical radiation. The portion of optical fiber with predetermined optical properties is adapted for producing two eigen modes of the optical radiation propagating therethrough with a predetermined optical path length difference.

The directional element is optically coupled with the delivering device and with the portion of optical fiber that has predetermined optical properties. The directional element is adapted for directing two replicas of the optical radiation to the proximal part of the delivering device. The two replicas propagate with an optical path length difference generally equal to the predetermined optical path length difference for the two eigen modes of the optical radiation. The delivering device is adapted for forming and delivering an optical radiation beam to an associated sample.

The delivering device includes a proximal part and a distal part, wherein the distal part of the delivering device includes a reference reflector. The reference reflector is adapted for producing a combination optical radiation by combining an optical radiation returning from an associated sample with a reference optical radiation reflected from the reference reflector. The delivering device is further adapted for delivering the combination optical radiation to the directional element. The directional element is further adapted for directing the combination optical radiation to the frequency domain optoelectronic registering unit.

In addition, the common path frequency domain optical coherence reflectometer of the present invention includes a frequency domain optoelectronic registering unit that includes a data processing and displaying unit, and is optically coupled with the directional element.

The common path frequency domain optical coherence reflectometer of the present invention is specified by an optical path length difference of a first value for the optical radiation beam propagating to the reference reflector and to the proximal boundary of a longitudinal range of interest and by an optical path length difference of a second value for the optical radiation beam propagating to the reference reflector and to the distal boundary of a longitudinal range of interest. The value of the optical path length difference for the two eigen modes of the optical radiation propagating through the portion of optical fiber with predetermined optical properties is, preferably, selected from the group consisting of: less than the first value, and exceeds the second value.

In accordance with another aspect of the present invention, the portion of optical fiber with predetermined optical properties is a portion of polarization maintaining optical fiber. Thus, the two eigen modes produced in the portion of polarization maintaining optical fiber are cross-polarization modes. In this embodiment, two replicas of optical radiation outgoing from the portion of polarization maintaining optical fiber are cross-polarized replicas of the optical radiation. The cross-polarized replicas propagate with an optical path length difference generally equal to the predetermined optical path length difference for the two eigen polarization modes of the optical radiation.

In one embodiment, the common path frequency domain optical coherence reflectometer includes a polarization controller placed between the source of optical radiation and the portion of polarization maintaining optical fiber. The polarization controller is adapted for controlling a power ratio between the two eigen polarization modes of the optical radiation propagating through the portion of polarization maintaining optical fiber.

In another embodiment, the common path frequency domain optical coherence reflectometer includes means adapted for modifying the two replicas outgoing from the portion of polarization maintaining optical fiber such, that the two replicas entering the directional element are parallel-polarized replicas of the optical radiation. The replicas propagate with an optical path length difference generally equal to the predetermined optical path length difference for the two eigen polarization modes of the optical radiation. The means adapted for modifying the two replicas is, preferably, implemented as a suitable polarizer. In this embodiment, a polarization controller is capable of being additionally included between the source of optical radiation and the portion of polarization maintaining optical fiber. The polarization controller is adapted for controlling a power ratio between the two eigen polarization modes of the optical radiation propagating through the portion of polarization maintaining optical fiber.

In accordance with another aspect of the present invention, the portion of optical fiber with predetermined optical properties is a portion of two mode optical fiber. In this embodiment, the two eigen modes produced in the portion of the two mode optical fiber are parallel-polarization modes. Thus, the two replicas of optical radiation outgoing from the portion of the two mode optical fiber are parallel-polarized replicas of the optical radiation. The parallel-polarized replicas propagate with an optical path length difference generally equal to the predetermined optical path length difference for the two parallel-polarization modes of the optical radiation.

The delivering device is, preferably, an optical fiber probe including an optical fiber extending therethrough. The optical fiber includes a tip placed in the distal part of the optical fiber probe. The tip of the optical fiber is suitably adapted for performing a function of a reference reflector.

In one preferred embodiment, the source of optical radiation is tunable. In this embodiment, the frequency domain optoelectronic registering unit includes at least one photodetector connected with the data processing and displaying unit.

In another preferred embodiment, the source of optical radiation is a low-coherence source of optical radiation. In this embodiment, the frequency domain optoelectronic registering unit includes a spectrometer connected with the data processing and displaying unit.

In yet another preferred embodiment, the common path frequency domain optical coherence reflectometer further includes means adapted for changing relative positions of the optical radiation beam being delivered to an associated sample, and an associated sample. In this embodiment, the common path frequency domain optical coherence reflectometer is part of a common path frequency domain device for optical coherence tomography.

In accordance with a further aspect of the present invention, there is provided a common path frequency domain optical coherence tomography device, specified by a longitudinal range of interest having a proximal boundary and a distal boundary, and at least partially overlapping with an associated sample. The common path frequency domain optical coherence tomography device includes a source of optical radiation, an optical fiber probe, and a directional element. The optical fiber probe is adapted for forming and delivering an optical radiation beam to an associated sample. The optical fiber probe includes a proximal part, a distal part, and an optical fiber extending therethrough. The optical fiber includes a tip placed in the distal part of the optical fiber probe. The tip of the optical fiber is adapted for performing a function of a reference reflector.

The common path frequency domain optical coherence tomography device also includes a portion of optical fiber with predetermined optical properties, which is optically coupled with the source of optical radiation. The portion of optical fiber with predetermined optical properties is adapted for producing two eigen modes of the optical radiation propagating therethrough with a predetermined optical path length difference. In one embodiment, the portion of optical fiber with predetermined optical properties is a portion of polarization maintaining optical fiber, wherein the two eigen modes produced in the portion of polarization maintaining optical fiber are cross-polarization modes. In another embodiment, the portion of optical fiber with predetermined optical properties is a portion of two mode optical fiber.

The directional element, included in the common path frequency domain optical coherence tomography device, is adapted for directing two replicas of the optical radiation, propagating with an optical path length difference generally equal to the predetermined optical path length difference for the two eigen modes of the optical radiation, to the proximal part of the optical fiber probe. The directional element is optically coupled with the optical fiber probe and with the portion of optical fiber with predetermined optical properties. In addition, the common path frequency domain optical coherence tomography device includes means adapted for changing relative positions of the optical radiation beam being delivered to an associated sample, and an associated sample. Also included in the common path frequency domain optical coherence tomography device is a frequency domain optoelectronic registering unit including a data processing and displaying unit, and optically coupled with the directional element.

Thus, in accordance with the subject invention, unlike previously known common path frequency domain OCT/OCR devices, optical radiation from a source is first split into two replicas by a portion of optical fiber with predetermined optical properties adapted for producing two eigen modes of the optical radiation propagating therethrough with a predetermined optical path length difference. The two replicas of the optical radiation outgoing from the portion of the optical fiber are then delivered to an associated sample by a delivering device, the delivering device being, preferably, an optical fiber probe. The tip of the optical fiber of the optical fiber probe serves as a reference reflector and also serves as a combining element that produces a combination optical radiation by combining an optical radiation returning from the associated sample with a reference optical radiation reflected from the reference reflector. The topology of the devices of the subject invention allows for registering a cross-polarized component of the optical radiation reflected or backscattered from the associated sample, as well as a parallel-polarized component. Having the optical path length difference for the two eigen modes of the optical radiation (which is an equivalent of an interferometer offset in previously known devices) differ from the reference offset in the common path frequency domain optical coherence reflectometry and optical coherence tomography devices of the present invention allows for relieving the requirements to the spectral resolution of the FD OCT engine and/or data acquisition and processing system, and substantially eliminates depth ambiguity problems.

Still other objects and aspects of the present invention will become readily apparent to those skilled in this art from the following description wherein there are shown and described preferred embodiments of this invention, simply by way of illustration of the best modes suited for to carry out the invention. As it will be realized by those skilled in the art, the invention is capable of other different embodiments and its several details are capable of modifications in various obvious aspects all without departing from the scope of the invention. Accordingly, the drawings and description will be regarded as illustrative in nature and not as restrictive.

BRIEF DESCRIPTION OF DRAWINGS

For a more complete understanding of the present invention and the advantages thereof, reference is now made to the following description taken in conjunction with the accompanying drawings, in which.

DETAILED DESCRIPTION OF THE INVENTION

The subject application is directed to systems and methods for visualizing subsurface regions of samples, and more specifically, to a frequency domain optical coherence reflectometer and frequency domain optical coherence tomography device that provide internal depth profiles and depth images of samples. Modifications of the common path frequency domain optical coherence reflectometer are illustrated by means of examples of optical fiber devices being part of an apparatus for optical coherence tomography, although it is evident that they may be implemented with the use of bulk optic elements, and may be used as independent devices. The optical fiber implementation is preferable for use in medical applications, especially in endoscopy, where flexibility of the optical fiber provides convenient access to different tissues and organs, including internal organs via an endoscope.

Figure 1:
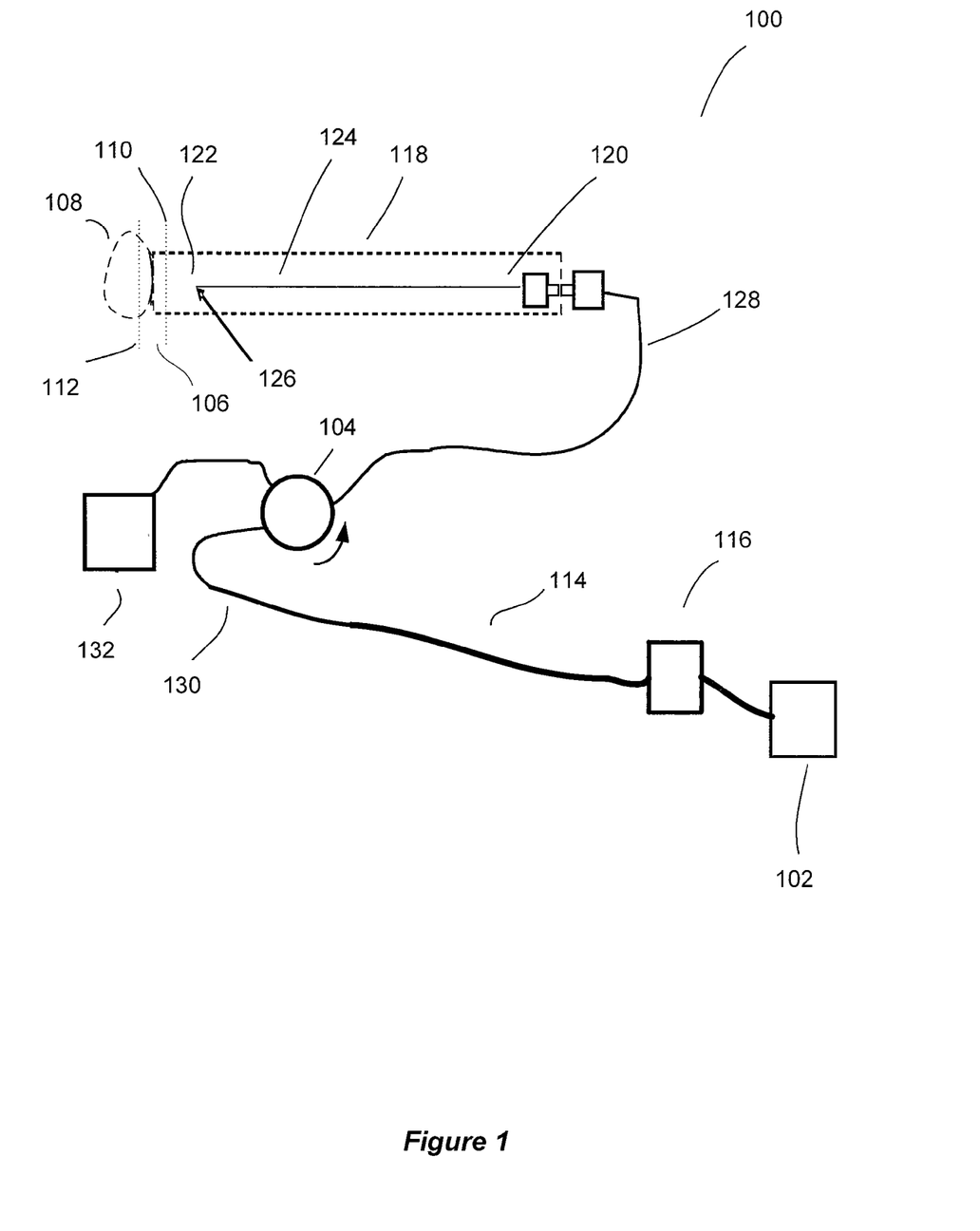
FIG. 1 is a block diagram of one preferred embodiment of the common path frequency domain optical coherence reflectometer in accordance with the subject application.

Turning now to FIG. 1, there is shown a block diagram of an embodiment of the common path frequency domain optical coherence reflectometer 100. As shown in FIG. 1, the reflectometer 100 includes a source 102 of optical radiation, and a directional element 104. In a preferred embodiment, the source 102 operates in the visible or near IR range. A skilled artisan will appreciate that the source 102 is, for example, and without limitation, a semiconductor superluminescent diode, doped-fiber amplified spontaneous emission superlum, solid state and fiberoptic femtosecond laser. A skilled artisan will also appreciate that directional element 104 is capable of being implemented as any suitable directional element known in the art.

The reflectometer 100 is specified by a longitudinal range of interest 106 at least partially overlapping with an associated sample 108. The longitudinal range of interest 106 has a proximal boundary 110 and a distal boundary 112. The common path frequency domain optical coherence reflectometer 100 also includes a portion of optical fiber with predetermined optical properties adapted for producing two eigen modes of the optical radiation propagating therethrough with a predetermined optical path length difference. This portion of optical fiber is illustrated in FIG. 1 as a portion of polarization maintaining optical fiber 114. The polarization maintaining optical fiber 114 is optically coupled with the source 102 of optical radiation.

The embodiment of the common path frequency domain optical coherence reflectometer 100 of FIG. 1 includes a polarization controller 116 placed between the source 102 of optical radiation and the polarization maintaining optical fiber 114. The polarization controller 116 is adapted for controlling a power ratio between the two eigen polarization modes of the optical radiation propagating through the polarization maintaining optical fiber 114. As will be understood by a skilled artisan, the polarization controller 116 is capable of being implemented as any suitable polarization controller known in the art.

The common path frequency domain optical coherence reflectometer 100 also includes a delivering device adapted for forming and delivering an optical radiation beam to an associated sample 108. In the embodiment of FIG. 1, the delivering device is implemented as an optical fiber probe 118 that includes a proximal part 120, a distal part 122, and an optical fiber 124 extending therethrough. The optical fiber 124 includes a tip 126 placed in the distal part 122 of the optical fiber probe 118. The tip 126 of the optical fiber 124 is adapted for performing a function of a reference reflector.

The directional element 104 is optically coupled with the optical fiber probe 118 and with the polarization maintaining optical fiber 114. In the embodiment illustrated in FIG. 1, the directional element 104 is optically coupled with the optical fiber probe 118 through an optical fiber 128, and is coupled with the polarization maintaining optical fiber 114 through an optical fiber 130. In the embodiment of FIG. 1, the directional element 104 is adapted for directing two replicas of the optical radiation to the proximal part of the optical fiber probe 118.

The common path frequency domain optical coherence reflectometer 100 of FIG. 1, is specified by an optical path length difference of a first value for the optical radiation beam propagating to the tip 126 of the optical fiber 124 and to the proximal boundary 110 of a longitudinal range of interest 106, and by an optical path length difference of a second value for the optical radiation beam propagating to the tip 126 of the optical fiber 124 and to the distal boundary 112 of a longitudinal range of interest 106. Those skilled in the art will recognize that the above mentioned predetermined optical properties of the polarization maintaining optical fiber 114 are chosen such, that the value of the optical path length difference for the two eigen modes of the optical radiation propagating through the polarization maintaining optical fiber 114 is, preferably, one of the following: less than the first value, and exceeds the second value.

The common path frequency domain optical coherence reflectometer 100 further includes a frequency domain optoelectronic registering unit 132 optically coupled with the directional element 104. The frequency domain optoelectronic registering unit 132 includes a data processing and displaying unit (not shown in the drawing). A skilled artisan will appreciate that the frequency domain optoelectronic registering unit 132 is capable of being implemented as any suitable registering unit known in the art.

Figure 2:
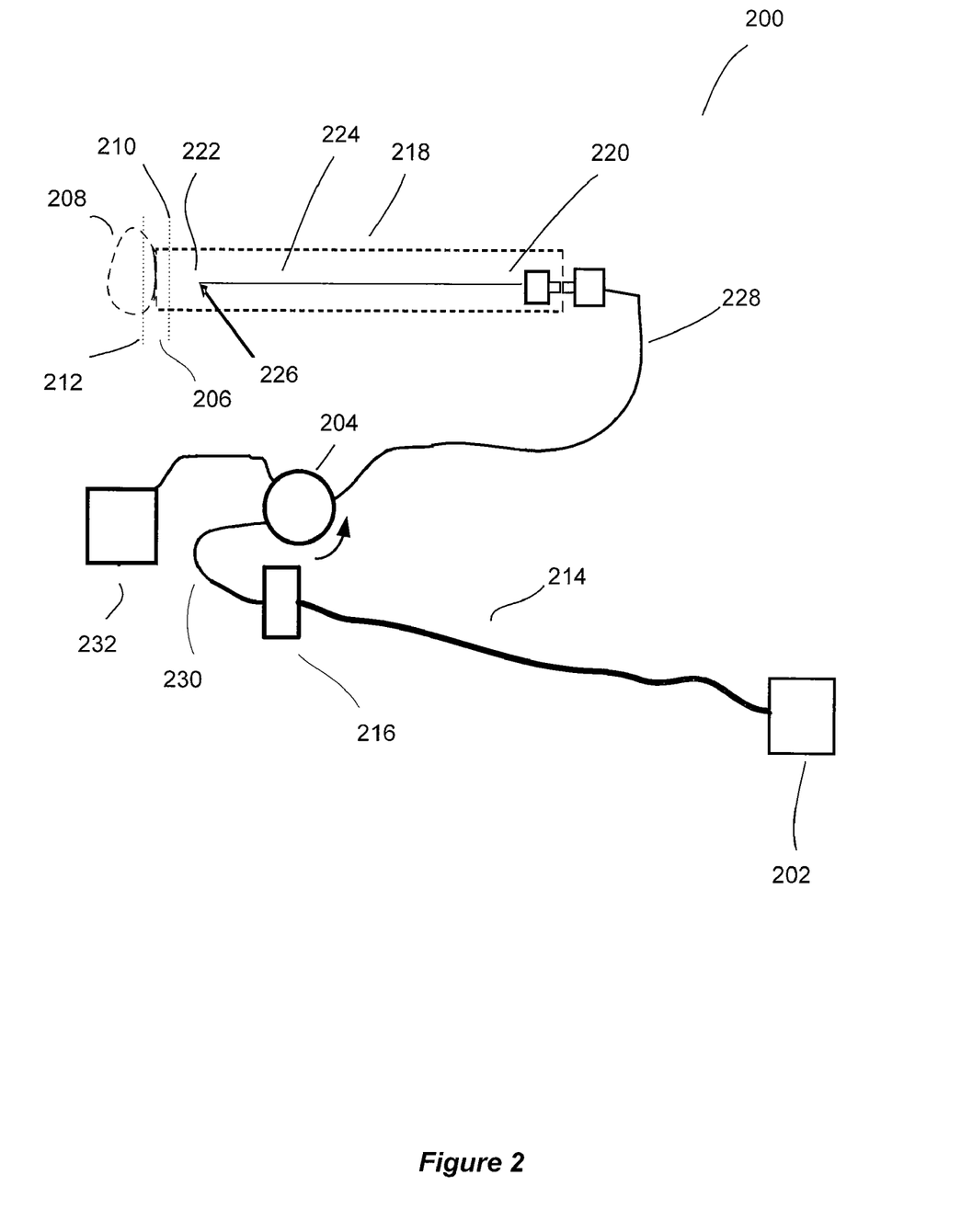
FIG. 2 is a block diagram of another preferred embodiment of the common path frequency domain optical coherence reflectometer in accordance with the subject application.

Turning now to FIG. 2, there is shown a block diagram of another embodiment of the common path frequency domain optical coherence reflectometer 200. As shown in FIG. 2, the reflectometer 200 includes a source 202 of optical radiation, and a directional element 204. A skilled artisan will appreciate that the source 202 and the directional element 204 are capable of being implemented analogous to respective elements referred to in the description of the embodiment shown in FIG. 1.

The reflectometer 200 is specified by a longitudinal range of interest 206 at least partially overlapping with an associated sample 208. The longitudinal range of interest 206 has a proximal boundary 210 and a distal boundary 212. The common path frequency domain optical coherence reflectometer 200 also includes a portion of optical fiber with predetermined optical properties adapted for producing two eigen modes of the optical radiation propagating therethrough with a predetermined optical path length difference. This portion of optical fiber is illustrated in FIG. 2 as a portion of polarization maintaining optical fiber 214. The polarization maintaining optical fiber 214 is optically coupled with the source 202 of optical radiation.

The embodiment of the common path frequency domain optical coherence reflectometer 200 of FIG. 2 includes means adapted for modifying the two replicas outgoing from the portion of polarization maintaining optical fiber 214 such, that the two replicas entering the directional element 204 are parallel-polarized replicas of the optical radiation. In the embodiment illustrated in FIG. 2, the means for modifying the two replicas is implemented as a polarizer 216 placed between the polarization maintaining optical fiber 214 and the directional element 204. The polarizer 216 is capable of being further adapted for controlling a power ratio between the two replicas of optical radiation. Alternatively, a polarization controller is capable of being additionally placed between the source of optical radiation 202 and the polarization maintaining fiber 214 (not shown in the drawing) for controlling a power ratio between the two replicas of optical radiation. As will be understood by a skilled artisan, the polarizer 216 is capable of being implemented as any suitable polarization controller known in the art. Preferably, the polarizer 216 is implemented as a 45 degree polarizer.

The common path frequency domain optical coherence reflectometer 200 also includes a delivering device adapted for forming and delivering an optical radiation beam to an associated sample 208. In the embodiment of FIG. 2, the delivering device is implemented as an optical fiber probe 218 that includes a proximal part 220, a distal part 222, and an optical fiber 224 extending therethrough. The optical fiber 224 includes a tip 226 placed in the distal part 222 of the optical fiber probe 218. The tip 226 of the optical fiber 224 is adapted for performing a function of a reference reflector.

The directional element 204 is optically coupled with the optical fiber probe 218 and with the polarization maintaining optical fiber 214. In the embodiment illustrated in FIG. 2, the directional element 204 is optically coupled with the optical fiber probe 218 through an optical fiber 228, and is coupled with the polarization maintaining optical fiber 214 through an optical fiber 230 and the polarizer 216. In the embodiment of FIG. 2, the directional element 204 is adapted for directing two replicas of the optical radiation to the proximal part of the optical fiber probe 218.

The common path frequency domain optical coherence reflectometer 200 of FIG. 1, is specified by an optical path length difference of a first value for the optical radiation beam propagating to the tip 226 of the optical fiber 224 and to the proximal boundary 210 of a longitudinal range of interest 206, and by an optical path length difference of a second value for the optical radiation beam propagating to the tip 226 of the optical fiber 224 and to the distal boundary 212 of a longitudinal range of interest 206. Those skilled in the art will recognize that the above mentioned predetermined optical properties of the polarization maintaining optical fiber 214 are chosen such, that the value of the optical path length difference for the two eigen modes of the optical radiation propagating through the polarization maintaining optical fiber 214 is, preferably, one of the following: less than the first value, and exceeds the second value.

The common path frequency domain optical coherence reflectometer 200 further includes a frequency domain optoelectronic registering unit 232 optically coupled with the directional element 204. The frequency domain optoelectronic registering unit 232 includes a data processing and displaying unit (not shown in the drawing). A skilled artisan will appreciate that the frequency domain optoelectronic registering unit 232 is capable of being implemented analogous to the frequency domain optoelectronic registering unit 132 of the embodiment illustrated in FIG. 1.

Figure 3:
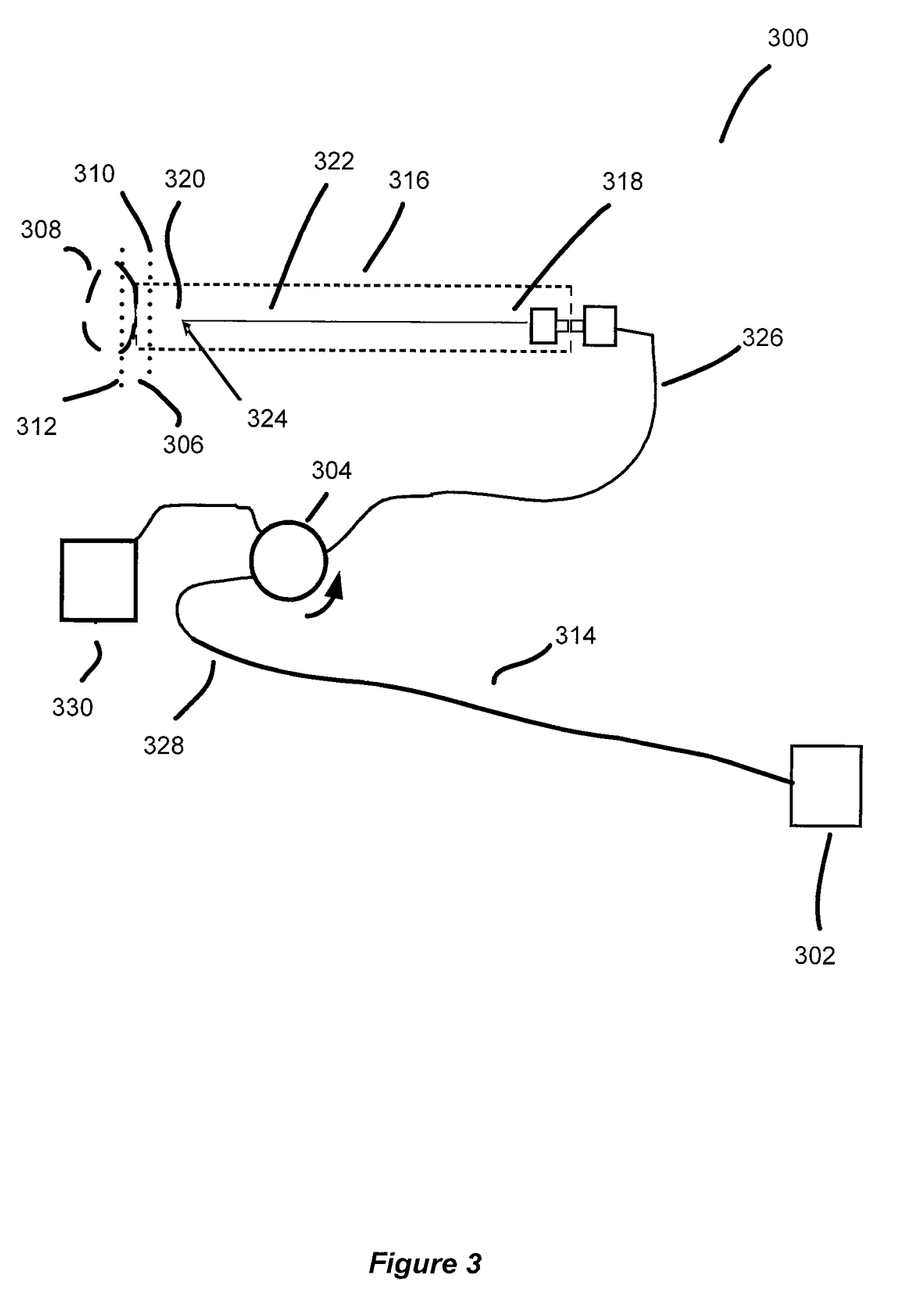
FIG. 3 is a block diagram of another preferred embodiment of the common path frequency domain optical coherence reflectometer in accordance with the subject application.

Turning now to FIG. 3, there is shown a block diagram of another embodiment of the common path frequency domain optical coherence reflectometer 300. As shown in FIG. 3, the reflectometer 300 includes a source 302 of optical radiation, and a directional element 304. A skilled artisan will appreciate that the source 302 and the directional element 304 are capable of being implemented analogous to the source 102 and directional element 104, respectively, of the embodiment shown in FIG. 1. The reflectometer 300 is specified by a longitudinal range of interest 306 at least partially overlapping with an associated sample 308. The longitudinal range of interest 306 has a proximal boundary 310 and a distal boundary 312.

The common path frequency domain optical coherence reflectometer 300 also includes a portion of optical fiber with predetermined optical properties adapted for producing two eigen modes of the optical radiation propagating therethrough with a predetermined optical path length difference. This portion of optical fiber is illustrated in FIG. 3 as a portion of two-mode optical fiber 314. Thus, the two eigen modes produced by the two-mode optical fiber 314 are parallel-polarization modes. The two-mode optical fiber 314 is optically coupled with the source 302 of optical radiation.

The common path frequency domain optical coherence reflectometer 300 also includes a delivering device adapted for forming and delivering an optical radiation beam to an associated sample 308. In the embodiment of FIG. 3, the delivering device is implemented as an optical fiber probe 316 that includes a proximal part 318, a distal part 320, and an optical fiber 322 extending therethrough. The optical fiber 322 includes a tip 324 placed in the distal part 320 of the optical fiber probe 316. The tip 324 of the optical fiber 322 is adapted for performing a function of a reference reflector.

The directional element 304 is optically coupled with the optical fiber probe 316 and with the two-mode optical fiber 314. In the embodiment illustrated in FIG. 3, the directional element 304 is optically coupled with the optical fiber probe 316 through an optical fiber 326, and is coupled with the two-mode optical fiber 314 through an optical fiber 328. In the embodiment of FIG. 3, the directional element 204 is adapted for directing two replicas of the optical radiation to the proximal part of the optical fiber probe 316.

The common path frequency domain optical coherence reflectometer 300 of FIG. 3, is specified by an optical path length difference of a first value for the optical radiation beam propagating to the tip 324 of the optical fiber 322 and to the proximal boundary 310 of a longitudinal range of interest 306, and by an optical path length difference of a second value for the optical radiation beam propagating to the tip 324 of the optical fiber 322 and to the distal boundary 312 of a longitudinal range of interest 306. Those skilled in the art will recognize, that the above mentioned predetermined optical properties of the two-mode optical fiber 314 are chosen such, that the value of the optical path length difference for the two eigen modes of the optical radiation propagating through the two-mode optical fiber 314 is, preferably, one of the following: less than the first value, and exceeds the second value.

The common path frequency domain optical coherence reflectometer 300 further includes a frequency domain optoelectronic registering unit 330 optically coupled with the directional element 304. The frequency domain optoelectronic registering unit 330 includes a data processing and displaying unit (not shown in the drawing). A skilled artisan will appreciate that the frequency domain optoelectronic registering unit 330 is capable of being implemented analogous to the frequency domain optoelectronic registering unit 132 of the embodiment illustrated in FIG. 1.

In accordance with another aspect of the invention, the embodiments of FIG. 1, FIG. 2, and FIG. 3 are capable of further including means for changing relative positions of the optical radiation beam being delivered to an associated sample, and the associated sample (not shown in the drawing). In this embodiment, the common path frequency domain optical coherence reflectometers illustrated in FIGS. 1 through 3 each are part of a common path frequency domain device for optical coherence tomography. Those skilled in the art will recognize, that in these devices the means for changing relative positions of the optical radiation beam being delivered to the associated sample, and the associated sample is suitably capable of being implemented in any way known in the art, for example and without limitation, as a lateral scanner incorporated into the delivering device, or as an element for changing the position of the associated sample.

Referring now to operation of the common path frequency domain optical coherence reflectometer 100 in accordance with the present invention shown in FIG. 1, the operation of the reflectometer 100 commences by placing the delivering device, preferably implemented as the optical fiber probe 118, at a predetermined position with respect to the sample 108. Depending basically on the tasks performed, the optical fiber probe 118 is placed in the vicinity of the sample 108, in contact with the sample 108, or at a predetermined distance from the sample 108. In all cases, there is a distance between the tip 126 of the optical fiber 124, the tip 126 serving as a reference reflector, and the proximal boundary 110 of the longitudinal range of interest 106, which is specified as an optical path length of a first value (reference offset). The distance between the tip 126 of the optical fiber 124 and the distal boundary 112 of the longitudinal range of interest 106, will be referred to here as an optical path length of a second value. Hence, in the preferred embodiment the tip 126 of the optical fiber 124 is positioned at a distance having a first optical length value from the proximal boundary 110 of the longitudinal range of interest 106 (reference offset), or, in other words, having a second optical length value from the distal boundary 112 of the longitudinal range of interest 106.

Next, an optical radiation from the source 102 is directed to the polarization maintaining optical fiber 114. Those skilled in the art will recognize that the polarization maintaining optical fiber 114 produces two eigen modes of the optical radiation propagating therethrough, which are cross-polarization modes of the optical radiation. As will be appreciated by a skilled artisan, the cross-polarization modes of the optical radiation experience an optical path length difference, which is defined by the optical properties of the polarization maintaining optical fiber 114. In one preferred embodiment, the value of this optical path length difference is less than the first optical path length value between the tip 126 of the optical fiber 124 and the proximal boundary 110 of the longitudinal range of interest 106 (reference offset). In another preferred embodiment, the value of this optical path length difference exceeds the second optical path length value between the tip 126 of the optical fiber 124 and the distal boundary 112 of the longitudinal range of interest 106.

Those skilled in the art will appreciate that the optical path length difference for the cross-polarization modes of the optical radiation is equivalent to an interferometer offset in a common path frequency domain reflectometer with a secondary interferometer. This optical path length difference is suitably adjusted in the process of manufacturing and assembling. A typical length range for the polarization maintaining optical fiber 114 is capable of being from several meters to several tens of meters. As will be recognized by those skilled in the art, the value of the optical path length difference for the cross-polarization modes of the optical radiation propagating in the polarization maintaining optical fiber 114, being less than the reference offset, or exceeding the distance from the tip 126 of the optical fiber 124 to the distal boundary 112 of the longitudinal range of interest 106, nonetheless stays in the vicinity of the value of the reference offset.

Thus, outgoing from the polarization maintaining optical fiber 114 are two replicas of the optical radiation propagating with an optical path length difference generally equal to the predetermined optical path length difference for the two eigen cross-polarization modes of the optical radiation. In the embodiment illustrated in FIG. 1, the two replicas enter the optical fiber probe 118 through the common optical fiber 130, the directional element 104, and the common optical fiber 128. The optical fiber probe 118 is adapted for forming and delivering an optical radiation beam to the associated sample 108. Thus, one part of a portion of the optical radiation beam corresponding to each replica is delivered to the associated sample 108 and is reflected or backscattered from it (the sample portion).

Another part of each portion of the optical radiation that enters the optical fiber probe 118 does not reach the associated sample 108, but is instead reflected at the tip 126 of optical fiber 124 of the optical fiber probe 118, at some distance from the associated sample 108 (the reference portion). Those skilled in the art will appreciate that due to the mentioned above relationship between the reference offset and the optical path length difference between the two replicas, the tip 126 of optical fiber 124 produces a combination optical radiation in a manner similar to that of the directional coupler in a previously known common path optical coherence reflectometer with a secondary interferometer. The tip 126 of optical fiber 124 combines an optical radiation returning from the associated sample 108 of one replica of optical radiation with a reference optical radiation being reflected from the tip 126 of the other replica.

The combination optical radiation returning from the optical fiber probe 118 is directed to a frequency domain optoelectronic registering unit 132 including a data processing and displaying unit (not shown in the drawing) by the directional element 104. The combination optical radiation is registered by the frequency domain optoelectronic registering unit 132. The optical spectrum of the combination optical radiation registered by the frequency domain optoelectronic registering unit 132, has all necessary information about the in-depth coherent reflection profile by including a component that is Fourier conjugate of the in-depth profile of the sample. Thus, the profile is extracted from Fourier transformation of the optical spectrum of the combined optical radiation by the data processing and displaying unit of the frequency domain optoelectronic registering unit 132. No depth ambiguity problem arises since the optical path difference for the interfering reference and any part of sample portion belonging to the longitudinal range of interest of the two replicas of the optical radiation is not reduced to zero.

As will be appreciated by those skilled in the art, since the two replicas of the optical radiation outgoing from the polarization maintaining optical fiber 114 are cross-polarized replicas, the frequency domain optoelectronic registering unit 132 registers a combination optical radiation responsive only to a portion of the reflected or backscattered optical radiation that is depolarized by the associated sample 108. The non-depolarized portion of the optical radiation reflected from the associated sample 108 does not produce interference fringes and is not registered.

In a preferred embodiment illustrated in FIG. 1, the polarization controller 116 controls a power ratio between the two eigen polarization modes of the optical radiation propagating through the portion of polarization maintaining optical fiber 114, and, hence between the two replicas of the optical radiation. Typically, a ratio of 1:1 is considered desirable.

In one embodiment, the source 102 of optical radiation is narrowband and tunable, whereas the frequency domain optoelectronic registering unit 132 includes at least one photodetector connected with the data processing and displaying unit (not shown in FIG. 1). In another embodiment the source 102 is broadband and implemented as a low-coherence source of optical radiation. In this embodiment a spectrometer instead of a single photodiode is used in the frequency domain optoelectronic registering unit 132, therefore parallel registration is performed instead of sequential.

Referring now to operation of the common path frequency domain optical coherence reflectometer 200 in accordance with the present invention shown in FIG. 2, those skilled in the art will recognize, that the operation of the reflectometer 200 proceeds, essentially, in the same manner as the operation of the reflectometer 100 depicted in FIG. 1, as described in detail above. However, the two replicas outgoing from the portion of polarization maintaining optical fiber 214 are modified by the polarizer 216 such, that the two replicas entering the directional element 204 are parallel-polarized replicas of the optical radiation.

The two parallel-polarized replicas propagate further with an optical path length difference generally equal to the predetermined optical path length difference for the two eigen cross-polarization modes of the optical radiation. In this embodiment, the frequency domain optoelectronic registering unit 232 registers a combination optical radiation responsive to a portion of the reflected or backscattered optical radiation that is not depolarized by the associated sample 208. The depolarized portion of the optical radiation reflected or backscattered from the associated sample 208 does not produce interference fringes and is not registered. As will be appreciated by those skilled in the art, the own axis of the polarizer 216 is capable of being oriented such, as to provide a desired power ratio between the two replicas of optical radiation. Alternatively, a desired power ratio between the two replicas of optical radiation is capable of being provided by suitably controlling a power ratio between the two eigen cross-polarization modes of the optical radiation propagating through the polarization maintaining optical fiber 214. The latter is achieved using a suitable polarization controller placed between the source of optical radiation 202 and the polarization maintaining fiber 214 (not shown in the drawing).

Referring now to operation of the common path frequency domain optical coherence reflectometer 300 in accordance with the present invention shown in FIG. 3, those skilled in the art will recognize, that the operation of the reflectometer 300 proceeds, essentially, in the same manner as the operation of the reflectometer 100 depicted in FIG. 1, as described in detail above. As will be appreciated by a skilled artisan, the two-mode optical fiber 314 produces two eigen modes of the optical radiation propagating therethrough, which are parrallel-polarization modes of the optical radiation.

Analogous to that described with reference to the common path frequency domain optical coherence reflectometer depicted in FIG. 1, and in FIG. 2, the optical spectrum of the combination optical radiation registered by the frequency domain optoelectronic registering unit 330, has all necessary information about the in-depth coherent reflection profile by including a component that is Fourier conjugate of the in-depth profile of the sample. Thus, the profile is extracted from Fourier transformation of the optical spectrum of the combined optical radiation by the data processing and displaying unit of the frequency domain optoelectronic registering unit 330. No depth ambiguity problem arises since the optical path difference for the interfering reference and any part of sample portion belonging to the longitudinal range of interest of the two replicas of the optical radiation is not reduced to zero.

In this embodiment, the frequency domain optoelectronic registering unit 330 registers a combination optical radiation responsive to a portion of the reflected or backscattered optical radiation that is not depolarized by the associated sample 308. The depolarized portion of the optical radiation reflected or backscattered from the associated sample 208 does not produce interference fringes and is not registered.

Figure 4A:
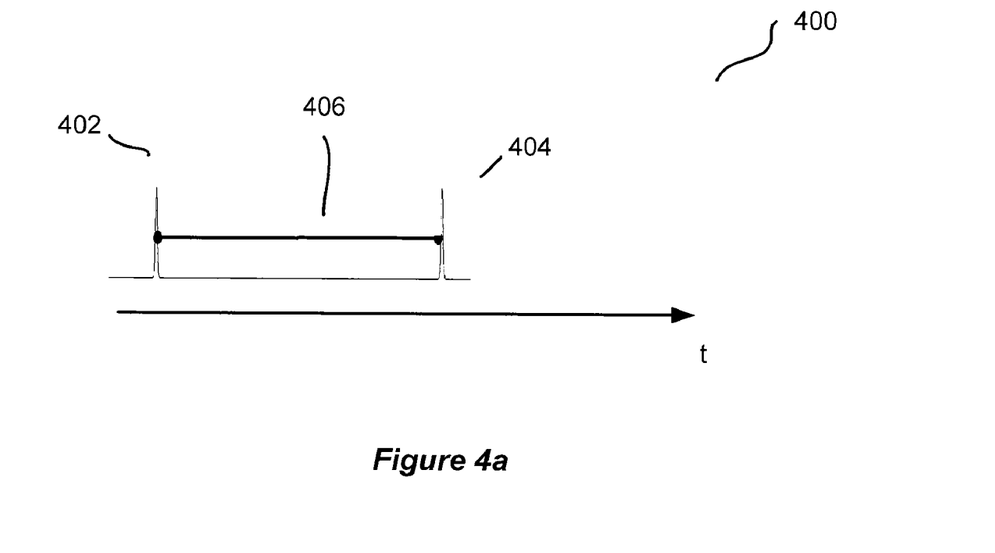
FIGS. 4a and 4b illustrate producing of a combination optical radiation in accordance with the subject application.

Turning now to FIG. 4, there is shown an illustration 400 of producing a combination optical radiation in an embodiment of the invention depicted in FIG. 1. For illustration purposes the optical radiation is represented by an imaginary short pulse propagating therethrough and placed along a time axis t in FIG. 4. Thus, FIG. 4a illustrates the optical radiation entering the optical fiber probe 118 through the directional element 104 of FIG. 1, after the optical radiation is divided into two replicas shifted along the time axis by the polarization maintaining fiber 114. The two replicas are illustrated in FIG. 4a as respective short pulses 402 and 404. As will be recognized by a skilled artisan, the time shift between the two replicas of the optical radiation is defined by the optical properties of the polarization maintaining fiber 114.

Figure 4B:
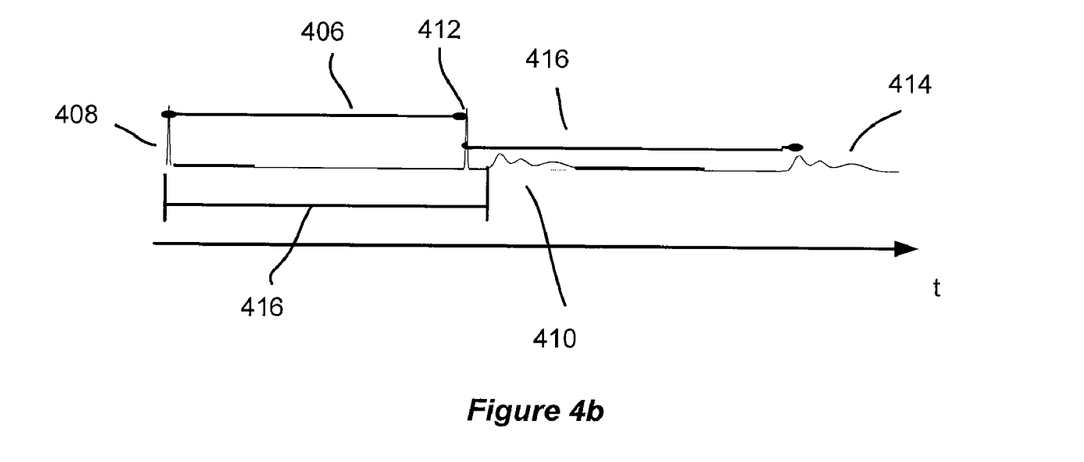

FIG. 4b illustrates the two replicas after each of them was split into two portions (a reference portion and a sample portion) by the tip 126 of the optical fiber 124 of the optical fiber probe 118. As shown in FIG. 4b, the reference portion 408 of the first replica has a shift (reference offset 416) with respect to the sample portion 410 of the same replica. Also, the reference portion 412 of the first replica has a shift (reference offset 416) with respect to the sample portion 414 of the same replica. Those skilled in the art will appreciate that reference portion of one replica interferes with the sample portion of the other replica.

A skilled artisan will understand, that the illustration provided in FIG. 4a and FIG. 4b for the embodiment of FIG. 1, is equally applicable to the embodiments of FIG. 2 and FIG. 3.

The foregoing description of the preferred embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed is:

1. A common path frequency domain optical coherence reflectometer specified by a longitudinal range of interest having a proximal boundary and a distal boundary, and at least partially overlapping with an associated sample, comprising:

a source of optical radiation;

a portion of optical fiber with predetermined optical properties optically coupled with the source of optical radiation, the portion of optical fiber with predetermined optical properties adapted for producing two eigen modes of the optical radiation propagating therethrough with a predetermined optical path length difference;

a delivering device adapted for forming and delivering an optical radiation beam to an associated sample, the delivering device comprising a proximal part and a distal part, the distal part of the delivering device including a reference reflector;

a directional element adapted for directing two replicas of the optical radiation, propagating with an optical path length difference generally equal to the predetermined optical path length difference for the two eigen modes of the optical radiation, to the proximal part of the delivering device, the directional element being optically coupled with the delivering device and with the portion of optical fiber with predetermined optical properties;

a frequency domain optoelectronic registering unit including a data processing and displaying unit, and optically coupled with the directional element;

wherein the reference reflector is adapted for producing a combination optical radiation by combining an optical radiation returning from an associated sample with a reference optical radiation reflected from the reference reflector;

wherein the delivering device is further adapted for delivering the combination optical radiation to the directional element, and wherein the directional element is further adapted for directing the combination optical radiation to the frequency domain optoelectronic registering unit.

2. The common path frequency domain optical coherence reflectometer of claim 1 further having an optical path length difference of a first value for the optical radiation beam propagating to the reference reflector and to the proximal boundary of a longitudinal range of interest, and having an optical path length difference of a second value for the optical radiation beam propagating to the reference reflector and to the distal boundary of a longitudinal range of interest, wherein the value of the optical path length difference for the two eigen modes of the optical radiation propagating through the portion of optical fiber with predetermined optical properties is selected from the group consisting of: less than the first value, and exceeds the second value.

3. The common path frequency domain optical coherence reflectometer of claim 1 wherein the portion of optical fiber with predetermined optical properties is a portion of polarization maintaining optical fiber, wherein the two eigen modes produced in the portion of polarization maintaining optical fiber are cross-polarization modes, and wherein two replicas of optical radiation outgoing from the portion of polarization maintaining optical fiber are cross-polarized replicas of the optical radiation propagating with an optical path length difference generally equal to the predetermined optical path length difference for the two eigen polarization modes of the optical radiation.

4. The common path frequency domain optical coherence reflectometer of claim 3 further comprising a polarization controller placed between the source of optical radiation and the portion of polarization maintaining optical fiber, wherein the polarization controller is adapted for controlling a power ratio between the two eigen polarization modes of the optical radiation propagating through the portion of polarization maintaining optical fiber.

5. The common path frequency domain optical coherence reflectometer of claim 3 further comprising means adapted for modifying the two replicas outgoing from the portion of polarization maintaining optical fiber such, that the two replicas entering the directional element are parallel-polarized replicas of the optical radiation propagating with an optical path length difference generally equal to the predetermined optical path length difference for the two eigen polarization modes of the optical radiation.

6. The common path frequency domain optical coherence reflectometer of claim 5 wherein the means adapted for modifying the two replicas outgoing from the portion of polarization maintaining optical fiber is a polarizer placed between the portion of polarization maintaining optical fiber and the directional element.

7. The common path frequency domain optical coherence reflectometer of claim 5 further comprising a polarization controller placed between the source of optical radiation and the portion of polarization maintaining optical fiber, wherein the polarization controller is adapted for controlling a power ratio between the two eigen polarization modes of the optical radiation propagating through the portion of polarization maintaining optical fiber.

8. The common path frequency domain optical coherence reflectometer of claim 1 wherein the portion of optical fiber with predetermined optical properties is a portion of two mode optical fiber, wherein the two eigen modes produced in the portion of two mode optical fiber are parallel-polarization modes, and wherein the two replicas outgoing from the portion of two mode optical fiber are parallel-polarized replicas of the optical radiation propagating with an optical path length difference generally equal to the predetermined optical path length difference for the two parallel-polarization modes of the optical radiation.

9. The common path frequency domain optical coherence reflectometer of claim 1 wherein the delivering device is an optical fiber probe comprising an optical fiber extending therethrough, the optical fiber including a tip placed in the distal part of the optical fiber probe.

10. The common path frequency domain optical coherence reflectometer of claim 9 wherein the tip of the optical fiber is adapted for performing a function of a reference reflector.

11. The common path frequency domain optical coherence reflectometer of claim 1 wherein the source of optical radiation is tunable, and wherein the frequency domain optoelectronic registering unit includes at least one photodetector connected with the data processing and displaying unit.

12. The common path frequency domain optical coherence reflectometer of claim 1 wherein the source of optical radiation is a low-coherence source of optical radiation, and wherein the frequency domain optoelectronic registering unit includes a spectrometer connected with the data processing and displaying unit.

13. The common path frequency domain optical coherence reflectometer of claim 1 further including means adapted for changing relative positions of the optical radiation beam being delivered to an associated sample, and an associated sample, wherein the common path frequency domain optical coherence reflectometer is part of a common path frequency domain device for optical coherence tomography.

14. A common path frequency domain optical coherence tomography device, specified by a longitudinal range of interest having a proximal boundary and a distal boundary, and at least partially overlapping with an associated sample, comprising:
a source of optical radiation;
a portion of optical fiber with predetermined optical properties optically coupled with the source of optical radiation, the portion of optical fiber with predetermined optical properties adapted for producing two eigen modes of the optical radiation propagating therethrough with a predetermined optical path length difference;
an optical fiber probe adapted for forming and delivering an optical radiation beam to an associated sample, the optical fiber probe comprising a proximal part, a distal part, and an optical fiber extending therethrough, the optical fiber including a tip placed in the distal part of the optical fiber probe, the tip of the optical fiber being adapted for performing a function of a reference reflector;
a directional element adapted for directing two replicas of the optical radiation, propagating with an optical path length difference generally equal to the predetermined optical path length difference for the two eigen modes of the optical radiation, to the proximal part of the optical fiber probe, the directional element being optically coupled with the optical fiber probe and with the portion of optical fiber with predetermined optical properties;
means adapted for changing relative positions of the optical radiation beam being delivered to an associated sample, and an associated sample;
a frequency domain optoelectronic registering unit including a data processing and displaying unit, and optically coupled with the directional element;
wherein the tip of the optical fiber of the optical fiber probe is further adapted for producing a combination optical radiation by combining an optical radiation returning from an associated sample with a reference optical radiation reflected from the tip of the optical fiber;
wherein the optical fiber probe is further adapted for delivering the combination optical radiation to the directional element, and
wherein the directional element is further adapted for directing the combination optical radiation to the frequency domain optoelectronic registering unit.

15. The common path frequency domain optical coherence tomography device of claim 14 further having an optical path length difference of a first value for the optical radiation beam propagating to the tip of the optical fiber of the optical fiber probe and to the proximal boundary of a longitudinal range of interest, and having an optical path length difference of a second value for the optical radiation beam propagating to the tip of the optical fiber of the optical fiber probe and to the distal boundary of a longitudinal range of interest, wherein the value of the optical path length difference for the two eigen modes of the optical radiation propagating through the portion of optical fiber with predetermined optical properties is selected from the group consisting of: less than the first value, and exceeds the second value.

16. The common path frequency domain optical coherence tomography device of claim 14 wherein the portion of optical fiber with predetermined optical properties is a portion of polarization maintaining optical fiber, wherein the two eigen modes produced in the portion of polarization maintaining optical fiber are cross-polarization modes, and wherein two replicas of optical radiation outgoing from the portion of polarization maintaining optical fiber are cross-polarized replicas of the optical radiation propagating with an optical path length difference generally equal to the predetermined optical path length difference for the two eigen polarization modes of the optical radiation.

17. The common path frequency domain optical coherence tomography device of claim 16 further comprising a polarization controller placed between the source of optical radiation and the portion of polarization maintaining optical fiber, wherein the polarization controller is adapted for controlling a power ratio between the two eigen polarization modes of the optical radiation propagating through the portion of polarization maintaining optical fiber.

18. The common path frequency domain optical coherence tomography device of claim 16 further comprising means adapted for modifying the two replicas outgoing from the portion of polarization maintaining optical fiber such, that the two replicas entering the directional element are parallel-polarized replicas of the optical radiation propagating with an optical path length difference generally equal to the predetermined optical path length difference for the two eigen polarization modes of the optical radiation.

19. The common path frequency domain optical coherence tomography device of claim 18 wherein the means adapted for modifying the two replicas outgoing from the portion of polarization maintaining optical fiber is a polarizer placed between the portion of polarization maintaining optical fiber and the directional element.

20. The common path frequency domain optical coherence tomography device of claim 18 further comprising a polarization controller placed between the source of optical radiation and the portion of polarization maintaining optical fiber, wherein the polarization controller is adapted for controlling a power ratio between the two eigen polarization modes of the optical radiation propagating through the portion of polarization maintaining optical fiber.

21. The common path frequency domain optical coherence tomography device of claim 14 wherein the portion of optical fiber with predetermined optical properties is a portion of two mode optical fiber, wherein the two eigen modes produced in the portion of two mode optical fiber are parallel-polarization modes, and wherein the two replicas outgoing from the portion of two mode optical fiber are parallel-polarized replicas of the optical radiation propagating with an optical path length difference generally equal to the predetermined optical path length difference for the two parallel-polarization modes of the optical radiation.

22. The common path frequency domain optical coherence tomography device of claim 14 wherein the source of optical radiation is tunable, and wherein the frequency domain optoelectronic registering unit includes at least one photodetector connected with the data processing and displaying unit.

23. The common path frequency domain optical coherence tomography device of claim 14 wherein the source of optical radiation is a low-coherence source of optical radiation, and wherein the frequency domain optoelectronic registering unit includes a spectrometer connected with the data processing and displaying unit.

* * * * *